United States Patent
Gupta et al.

(10) Patent No.: US 8,747,911 B2
(45) Date of Patent: Jun. 10, 2014

(54) BACTERIOSTATIC CATHETER LOCK CONTAINING GLYCEROL

(75) Inventors: Nisha Gupta, Audobon, PA (US); Elaine Steinke, Morgantown, PA (US); Erin Peters, Hamburg, PA (US); Joel Rosenblatt, Pottstown, PA (US)

(73) Assignee: Teleflex Medical Incorporated, Durham, NC (US)

(*) Notice: Subject to any disclaimer, the term of this patent is extended or adjusted under 35 U.S.C. 154(b) by 451 days.

(21) Appl. No.: 12/693,706

(22) Filed: Jan. 26, 2010

(65) Prior Publication Data

US 2010/0191219 A1    Jul. 29, 2010

Related U.S. Application Data

(60) Provisional application No. 61/147,671, filed on Jan. 27, 2009.

(51) Int. Cl.
*A61K 33/14*    (2006.01)

(52) U.S. Cl.
USPC ......................................................... 424/680

(58) Field of Classification Search
None
See application file for complete search history.

(56) References Cited

U.S. PATENT DOCUMENTS

| | | | | |
|---|---|---|---|---|
| 4,929,242 | A * | 5/1990 | Desecki et al. | 604/266 |
| 6,135,943 | A * | 10/2000 | Yu et al. | 600/16 |
| 6,958,049 | B1 | 10/2005 | Ash | |
| 7,132,413 | B1 | 11/2006 | Pfirrmann | |
| 7,696,182 | B2 * | 4/2010 | Prosl | 514/56 |
| 2005/0215978 | A1 | 9/2005 | Ash | |
| 2006/0177477 | A1 | 8/2006 | Ash et al. | |

FOREIGN PATENT DOCUMENTS

WO    WO 00/10385    3/2000

OTHER PUBLICATIONS

Garland, J.S., et al. "A Vancomycin-Heparin Lock Solution for Prevention of Nosocomial Bloodstream Infection in Critically Ill Neonates . . . ," Pediatrics 116: e198-205, 2005.
Weijmer, M.C., et al. "Randomized, Clinical Trial Comparison of Trisodium Citrate 30% and Heparin as Catheter-Locking Solution . . . ," J.Am.Soc.Nephrol 16: 2769-2777, 2005.
Opilla, M.T., et al. "Use of Ethanol Lock Therapy to Reduce the Incidence of Catheter-Related Bloodstream Infections . . . ," JPEN J.Parenter.Enteral.Nutr. 31:302-305, 2007.
Luo, Y.S., et al. "Comparison of Catheter Lock Solutions in Rats," 51st Annual Meeting of American Assoc. for Laboratory Animal Science, San Diego, CA, 2000.
Saegeman, V., et al. "Short- and Long-Term Bacterial Inhibiting Effect of High Concentrations of Glycerol Used in the Preservation of Skin . . . ," Burns 34:205-211, 2008.
Anonymous., "Guidance on 510 (k) Submissions for Implanted Infusion Ports", Feb. 27, 1997, pp. 1-27, Retrieved from the Internet: http://www.fda.gov/downloads/MedicalDevices/DeviceRegulationandGuidance/GuidanceDocunnents/UCM081374.pdf.
G. Boden et al., "In Vivo Effects of Insulin and Free Fatty Acids on Matrix Metalloproteinases in Rat Aorta", Diabetes, vol. 57, No. 2, Nov. 19, 2007, pp. 476-483.
Supplementary European Search Report for Application No. 10736287.3, filed Jan. 26, 2010.

* cited by examiner

*Primary Examiner* — Anand Desai
*Assistant Examiner* — Melissa Mercier
(74) *Attorney, Agent, or Firm* — Baker & Hostetler LLP

(57) ABSTRACT

A catheter lock composition for preventing bacterial infection having an effective amount of glycerol and sodium chloride solution. The effective amount of glycerol is between about 35-60% and sodium chloride is in a concentration range between 0.5-0.9%. The composition further includes an anticoagulant and/or an antimicrobial agent.

6 Claims, 9 Drawing Sheets ically disposed to glycerol. The solution provides enhanced anticoagulant effects.

BACTERIOSTATIC CATHETER LOCK CONTAINING GLYCEROL

CROSS-REFERENCE TO RELATED APPLICATIONS

This application claims priority to provisional U.S. patent application filed Jan. 27, 2009, having a Ser. No. 61/147,671, the disclosure of which is hereby incorporated by reference in its entirety.

FIELD OF THE INVENTION

The present invention relates generally to an antibacterial composition. More particularly, the present invention relates to an antibacterial composition and methods for flushing a medical device having a lumen.

BACKGROUND OF THE INVENTION

This invention relates to a composition that is used in connection with medical devices having a lumen, such as catheters.

Implanted catheters are used in a number of medical procedures. Intravenous (IV) therapy relies on long-term implantation of a venous catheter to deliver fluids, medications, and other substances to a patient. Hemodialysis and hemofiltration both rely on separate draw and return catheters implanted in a vein to allow extra-corporeal treatment of the blood.

Problems arise when catheters are implanted in the patient for an extended amount of time. The catheters can become infected, thus requiring treatment of the patient and removal of the catheter. Furthermore, implanted catheters can often become glugged or fouled over time. This is a particular problem with intravascular catheters where clotting and thrombus are formed within the catheter lumen.

Accordingly, it is desirable to provide an antimicrobial and anticoagulant catheter capable of overcoming the disadvantages described herein at least to some extent.

SUMMARY OF THE INVENTION

The foregoing needs are met, to a great extent, by the present invention, wherein in one respect a composition for a catheter lock solution with unexpected bacteriostatic as well as enhanced anticoagulant effects is provided.

An embodiment of the present invention pertains to a catheter lock solution with an effective amount of glycerol and a sodium chloride solution. The effective amount of glycerol is in a concentration range between about 35-60%. The sodium chloride is in a concentration range between about 0.5-0.9%. The catheter lock solution can include an anticoagulant and an antimicrobial agent.

Another embodiment of the present invention relates to a method for preventing infection of a patient having an indwelling intravascular catheter. The method includes infusing a lock solution into a lumen of the catheter. The lock solution includes glycerol in a concentration range between about 35-60% and sodium chloride in a concentration range between about 0.5-0.9%. The method includes placing a cap at an external end of the catheter. The catheter lock solution can include an anticoagulant and an antimicrobial agent.

Yet another embodiment of the present invention pertains to a kit. The kit includes a catheter having at least one lumen, a syringe, and a catheter lock solution. The catheter lock solution includes an effective amount of glycerol and sodium chloride solution.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
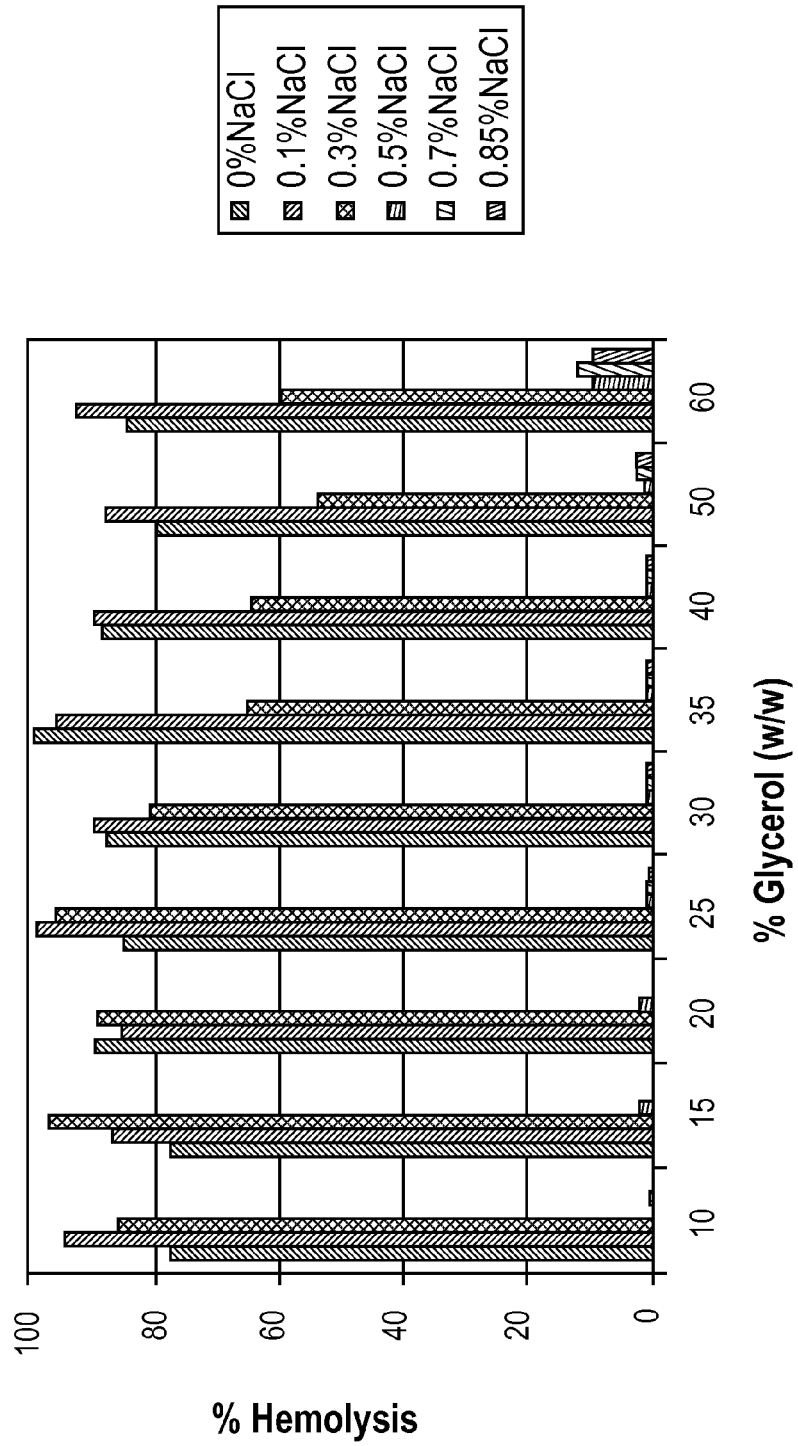
FIG. 1 is a chart showing hemocompatibility of catheter lock solutions containing varying concentration of glycerol and salt.

Embodiments of the invention provide a catheter lock solution for preventing bacterial infection. The catheter lock solution includes an effective amount of glycerol and a saline solution. The effective amount of glycerol is in a concentration range between about 35-60%. The effective amount of sodium chloride is in a concentration range between about 0.5-0.9%. In this composition, glycerol is used as an bactericidal agent that can be used to lock an indwelling vascular device, such as a central venous catheter, to prevent bacterial infection and thrombotic occlusions. The synergistic use of an effective amount of glycerol and sodium chloride solution balances hemocompatibility and antimicrobial effects. In accordance with an embodiment of the present invention, the effective amount of glycerol acts as an antimicrobial agent that initially causes bacterial stasis, and eventually becomes bactericidal. Furthermore, the catheter lock solution according to the present invention also improves the hemocompatibility by minimizing hemolysis and prolonging the clotting time.

The catheter lock solution can further include an anticoagulant. As employed herein, the term "anticoagulant" is intended to mean any composition that has the ability, either directly or indirectly, to prevent the coagulation of blood or to dissolve blood clots or other coagulated species once formed. Any compound known to have this capability can be employed. Examples of such compounds may include heparin, di-ammonium hydrogen citrate, di-ammonium tartrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N',N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, warfarin, acetylsalicylic acid, ibuprofen, indomethacin, prostaglandins, sulfinpyrazone, streptokinase, urokinase, tissue plasminogen activator (TPA), coumarin, protamine sulfate, anti-thrombin III, coumadin, protein C/protein S, nicoumalone, phenprocoumon, hirudin, hirulog, and the like. Mixtures of the foregoing can be employed.

The catheter lock solution can also include compounds of agents that prevent infection (e.g., antimicrobial agents and antibiotics), chemotherapeutic agents, antiseptics, antimicrobial dyes, or other biocides. The compounds of agents used with the composition can include, inter alia, a member selected from the group consisting of hydrochloric acid, a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate, imidazoline biocides, acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver, nanosilver, silver sulfadiazine, silver nitrate, 5 fluorouracil, phenolic antiseptics, gentian violet, methylene blue, brilliant green, and bismuth compounds.

Methods and Results

In operation, a care provider can infuse the catheter lock composition having an effective amount of glycerol in a saline solution to a lumen of an indwelling intravascular catheter. Upon displacing the body fluid inside the lumen with the catheter lock solution, the care provider can place a cap at an external end of the catheter. The lumen space is thereby made inhospitable to microorganisms and prevents the clotting of residual blood in the device.

Kit:

The invention further includes kits for preventing infection of a patient having an indwelling intravascular catheter. In an embodiment according to the present invention, the kit includes a catheter having at least one lumen, a syringe, and a catheter lock solution comprising an effective amount of glycerol and sodium chloride solution. The syringe can be used to draw the catheter lock solution and displace the body fluid inside the lumen of the catheter with the catheter lock solution.

Example 1

Preparation of Catheter Lock Solutions

Solutions containing 10%-60% glycerol (w/w) and 0.1%-0.85% sodium chloride (NaCl, w/v) were prepared in deionized water. Effect of these solutions alone, and in combination with Heparin lock (1000 units/mL heparin from bovine intestinal mucosa, supplied by Sigma-Aldrich of St. Louis, Mo. 63103 U.S.A. ("Sigma")) or Citrate Lock (3.8% sodium citrate) was evaluated in the hemolysis, microbiology and prothrombin clotting time assays.

Example 2

Hemocompatibility of Catheter Lock Solution as Determined by Hemolysis Assay

Method: Human blood is collected in 3.8% sodium citrate followed by centrifugation at 800 g for 15 min. The plasma fraction is collected in a separate tube to determine the total free hemoglobin, followed by 1× dilution of the red blood cells (RBC) fraction in 0.85% saline and centrifugation at 800 g for 15 min. The top layer is discarded and the washed RBC fraction is collected for further test. An aliquot of 20 ul of the RBC is mixed in 480 ul of a test solution, incubated for 1 hour at 37° C. on a rotator at speed 3. Each test solution contains varying concentration of glycerol (10-60%) and saline (0.1-0.85%). The solution is then centrifuged at 13,000 rpm on the micro-centrifuge. A 100 ul aliquot from the supernatant is used to read the absorbance at 541 nm on a plate reader.

FIG. 1 shows the results of hemocompatibility of catheter lock solutions containing varying concentrations of glycerol and salt. The catheter lock solutions containing 10-50% glycerol and 0.5-0.85% NaCl maintained the osmotic balance effectively across the RBC membrane and did not cause hemolysis. Solutions containing glycerol at 60% or higher concentration caused significant hemolysis even in the presence of physiologic 0.85% salt concentration.

Example 3

Antimicrobial Effect of Glycerol as Determined by "Time to Kill" Assay

The antimicrobial effect of glycerol was evaluated by testing against three common catheter-related blood stream infectious organisms: *Acinetobacter baumannii* ATCC 19606, *Enterobacter cloacae* ATCC 13047, and *Pseudomonas aeruginosa* ATCC 27853.

To determine the antimicrobial dose of glycerol and the time glycerol takes to kill the planktonic bacteria, solutions containing 10-50% glycerol (w/w) and 0.85% NaCl (w/v) were challenged with $1-5 \times 10^5$ colony forming units (CFU)/mL of planktonic bacteria. Following the challenge, bacterial growth in different solutions was monitored at time points 0, 24, and 48 hours, both by reading the absorbance at 670 nm, and by plating onto the Day Engle Agar plates and counting the number of colonies formed.

The absorbance data showed that there was no growth of bacteria in the solutions containing 30% or higher concentration of glycerol and 0.85% NaCl. Therefore, this indicates that solutions containing 30% or higher concentration of glycerol and 0.85% saline were bacteriostatic.

Figure 2A:
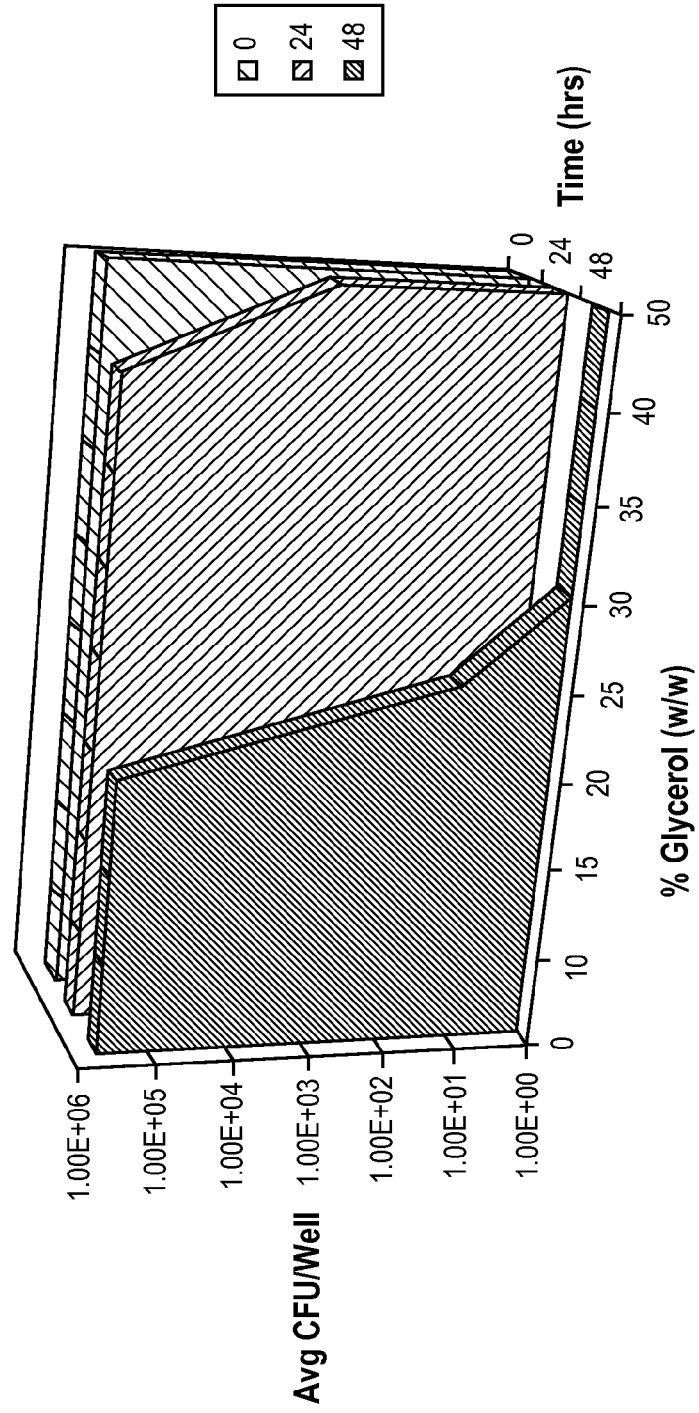
FIG. 2a is a chart showing the antimicrobial effect of solutions containing 0.85% NaCl and 10-50% glycerol on planktonic *Acinetobacter baumannii* at 0, 24, and 48 hours.
Figure 2B:
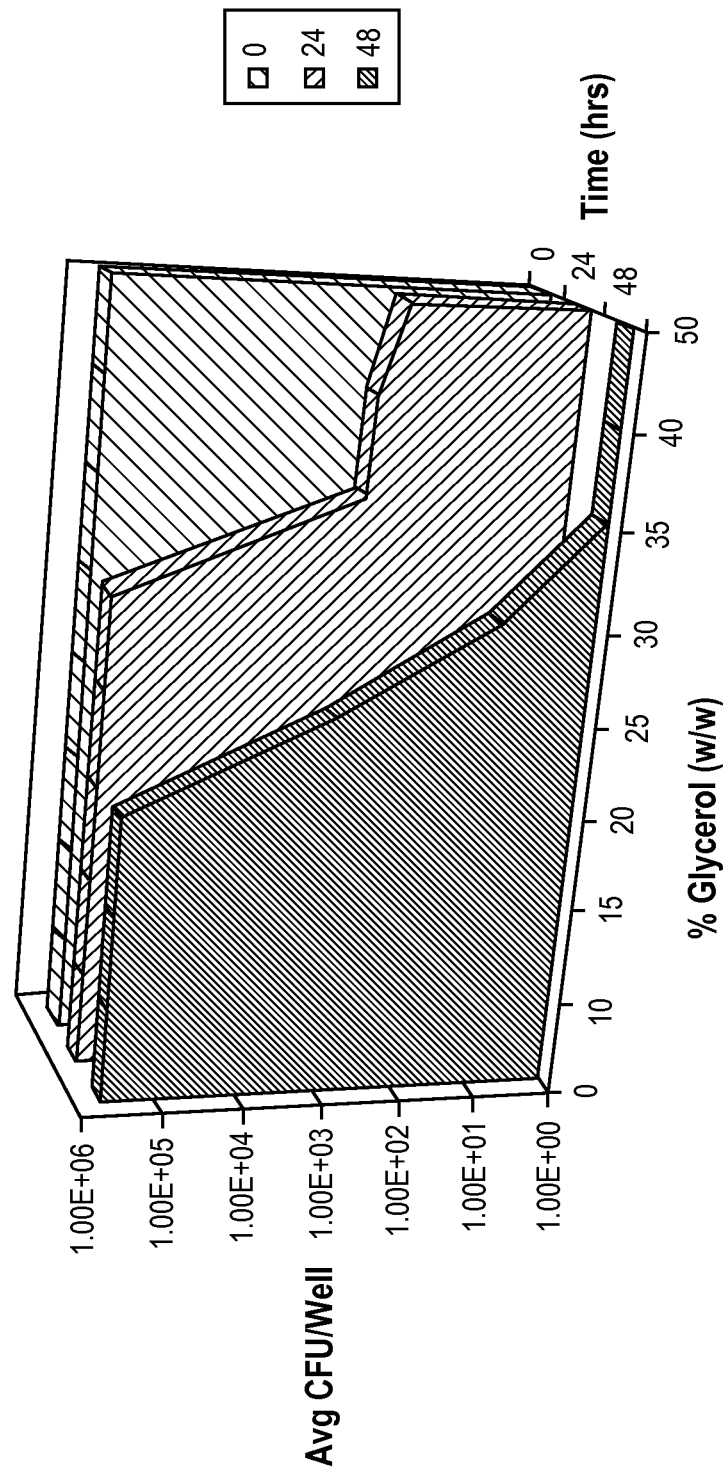
FIG. 2b is a chart showing the antimicrobial effect of solutions containing 0.85% NaCl and 10-50% glycerol on planktonic *Enterobacter colacae* at 0, 24, and 48 hours.
Figure 2C:
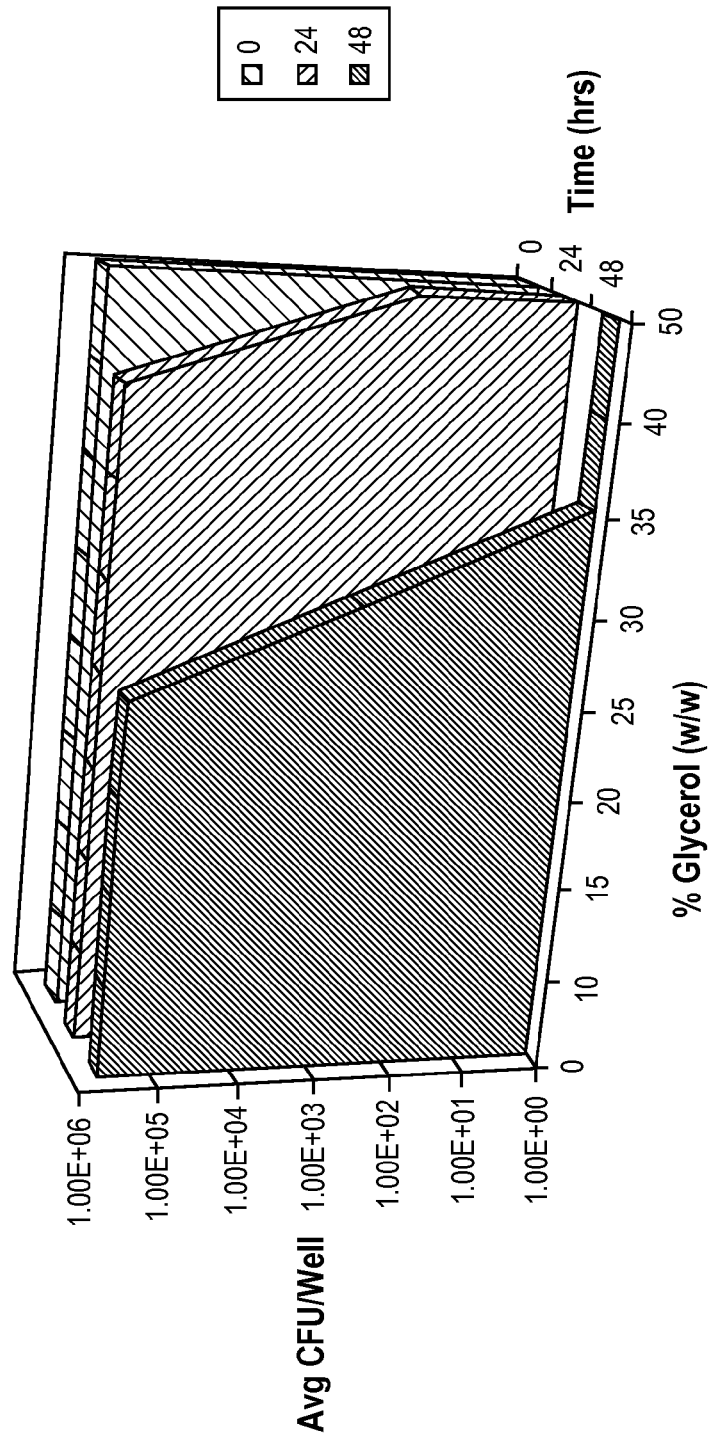
FIG. 2c is a chart showing the antimicrobial effect of solutions containing 0.85% NaCl and 10-50% glycerol on planktonic *Pseudomonas aeruginosa* at 0, 24, and 48 hours.

To confirm if the glycerol containing solutions were eventually bactericidal or not, solutions were plated on Day Engle Agar plates and the number of colonies formed were counted after 0, 24 and 48 hours. FIGS. 2a, 2b, and 2c show that there were no colonies formed when bacteria were challenged for more than 24 hours by the solutions containing 35% or higher concentration of glycerol. Thus, solutions at this concentration were effective against all three strains of microorganisms tested.

Example 4

Effect of Glycerol and Salt Concentration on Heparin Activity as Determined by Thrombin Clotting Time in Citrated Human Plasma or Whole Blood Method for plasma samples: Citrated human plasma (pooled) was mixed with 20 mM $CaCl_2$, 2480 Imidazole buffer solution (IBS) buffer (30 mM Tris-HCl pH8.4, 30 mM imidazole, 130 mM NaCl), and 10 µl of the test solution. Time to clot formation was recorded after the addition of five units of human thrombin (Sigma).

Method for whole blood samples: Fresh human blood was drawn into collection tubes containing 3.8% sodium citrate, and used within 3 hours. 100 ul of whole blood was mixed with 200 mM $CaCl_2$ and 20 µl of test solution. All tested samples contained 0.85% NaCl. Time to clot was measured after the addition of 3 Units of human thrombin (Sigma).

As shown in Table 1, the clotting time was prolonged by 7-10 seconds when glycerol was added to the normal saline solution containing 0.85% NaCl. This, indicates that the combination of glycerol and normal saline is more hemocompatible than just saline solution.

TABLE 1

Thrombin clotting time for plasma samples

| SAMPLES | Time to clot (seconds) | | |
|---|---|---|---|
| Plasma alone | 20 | | |
| 0.85% NaCl | 21 | | |
| 0.85% NaCl + heparin (1000 U/ml) | >48 hr | | |

| | % NaCl (w/v) | | |
|---|---|---|---|
| | 0.50% | 0.70% | 0.85% |
| 10% glycerol | 21 | 28 | 28 |
| 15% glycerol | 23 | 26 | 28 |
| 20% glycerol | 21 | 25 | 28 |
| 25% glycerol | 23 | 25 | 30 |
| 30% glycerol | 23 | 26 | 31 |
| 35% glycerol | 23 | 28 | 31 |
| 40% glycerol | 24 | 27 | 30 |
| 50% glycerol | 26 | 28 | 31 |
| 60% glycerol | 28 | 27 | 32 |
| 10% glycerol + heparin | >48 hr | >48 hr | >48 hr |
| 15% glycerol + heparin | >48 hr | >48 hr | >48 hr |
| 20% glycerol + heparin | >48 hr | >48 hr | >48 hr |
| 25% glycerol + heparin | >48 hr | >48 hr | >48 hr |
| 30% glycerol + heparin | >48 hr | >48 hr | >48 hr |
| 35% glycerol + heparin | >48 hr | >48 hr | >48 hr |
| 40% glycerol + heparin | >48 hr | >48 hr | >48 hr |
| 50% glycerol + heparin | >48 hr | >48 hr | >48 hr |
| 60% glycerol + heparin | >48 hr | >48 hr | >48 hr |

Furthermore as shown in Table 2, addition of glycerol to the heparin lock, at 20% or higher concentration prolonged the clotting time considerably in the whole blood assays. A combination of glycerol, 0.85% saline and heparin, therefore, is a more hemocompatible formulation for a catheter lock application than the saline or heparin lock solutions.

TABLE 2

Thrombin clotting time for plasma samples

| SAMPLES | Time to clot (minutes) |
|---|---|
| Whole Blood (WB) Only | 3 |
| Heparin (1000 U/ml) | 7 |
| 10% glycerol + heparin | 5 |
| 20% glycerol + heparin | >10 |
| 30% glycerol + heparin | >10 |
| 40% glycerol + heparin | >10 |
| 50% glycerol + heparin | >10 |
| 60% glycerol + heparin | >10 |

Example 5

Hemocompatibility of Catheter Lock Solution Containing Glycerol, Salt with either Heparin or Sodium Citrate as Determined by Hemolysis Assay Both Heparin and sodium citrate are commonly used anticoagulants. In this experiment, we wanted to determine the effect on hemocompatibility of the combination of glycerol, saline and these anticoagulants in comparison to the glycerol and saline combination (as in Example 2).

Solutions containing 10-60% glycerol with either 0.5% or 0.85% NaCl were evaluated for their hemocompatibility in presence of either 1000 units/mL Heparin or 3.8% sodium citrate by hemolysis method as described in Example 2.

Figure 3A:
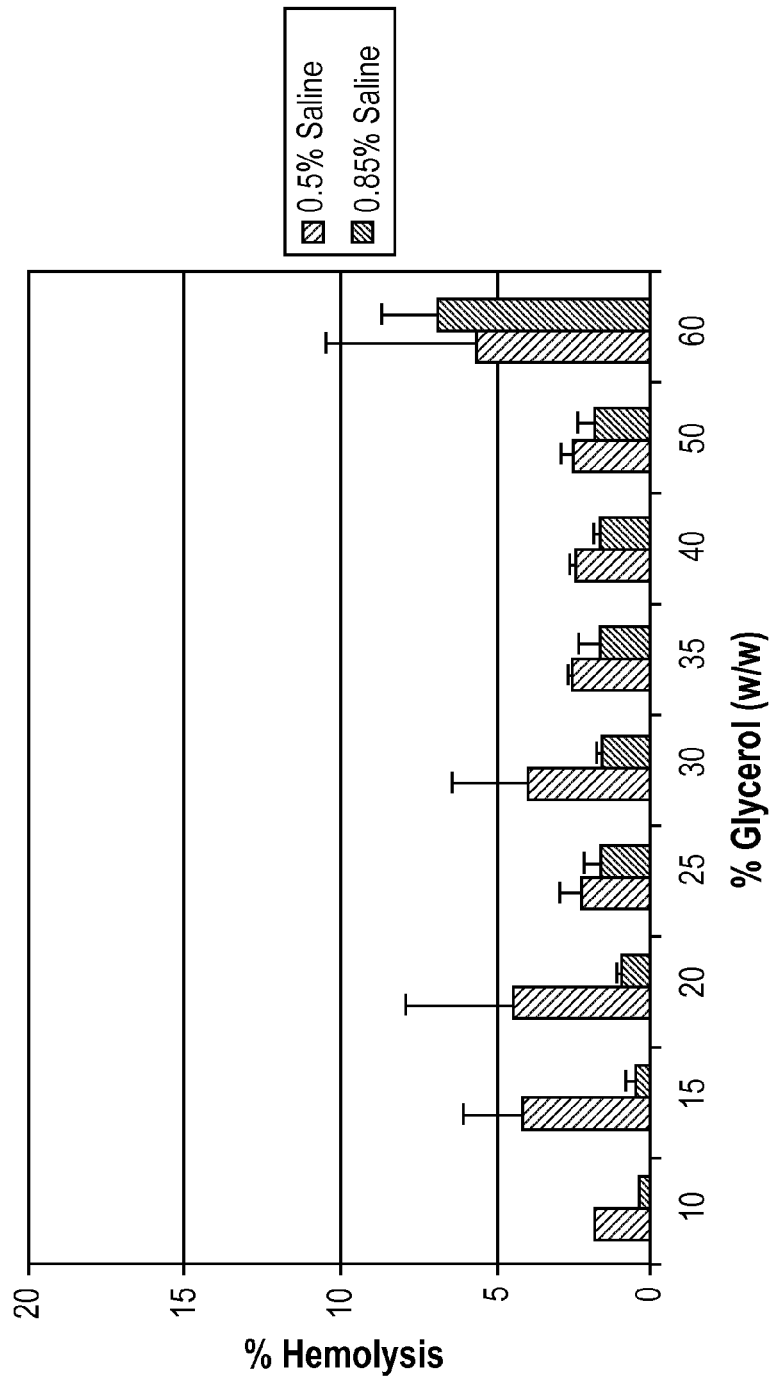
FIG. 3a is a chart showing the hemocompability of catheter lock solutions containing different concentrations of glycerol with either 0.5% or 0.85% saline in the presence of 1000 units/mL Heparin.
Figure 3B:
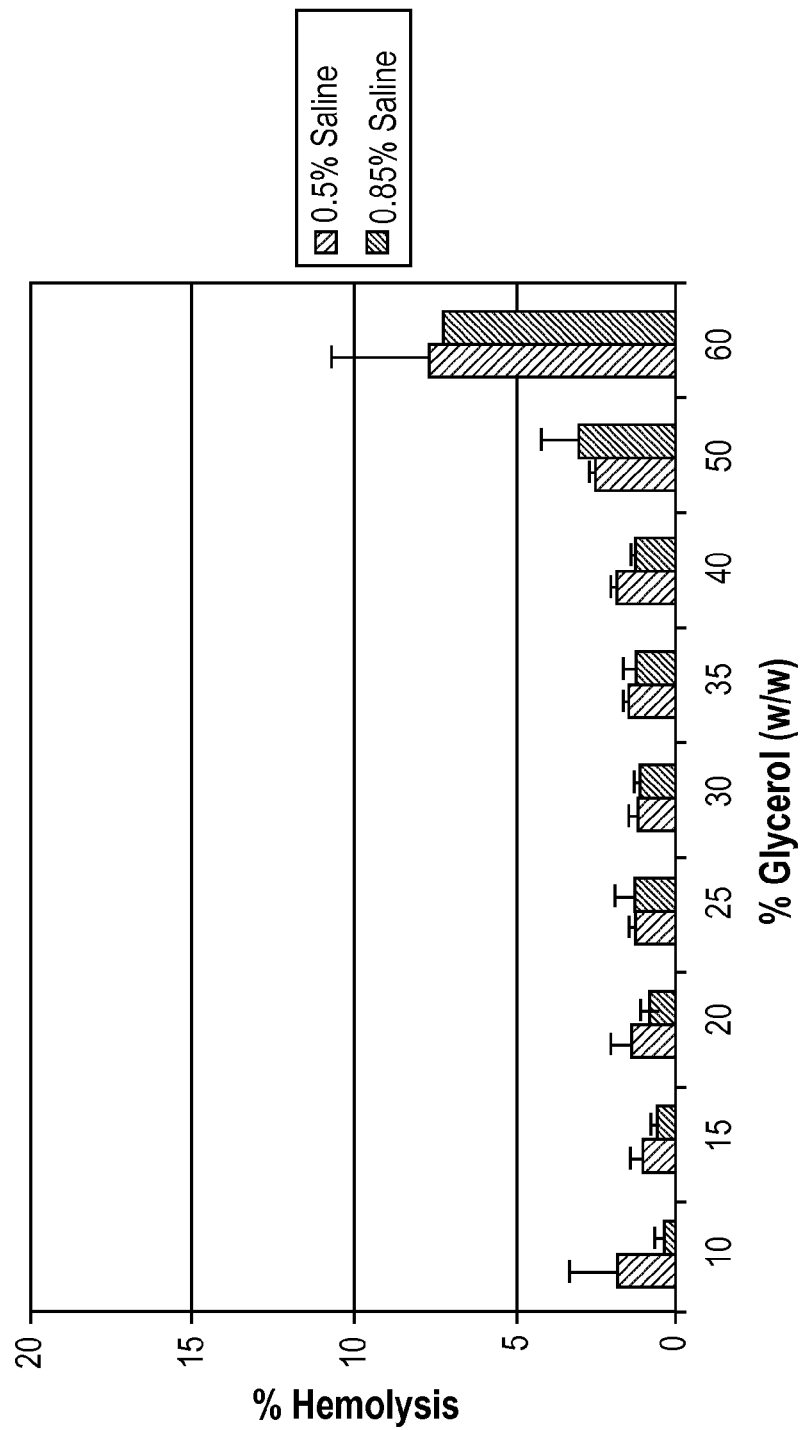
FIG. 3b is a chart showing the hemocompability of catheter lock solutions containing different concentrations of glycerol with either 0.5% or 0.85% saline in the presence of 3.8% of sodium citrate.

FIG. 3a shows the hemocompatibility of catheter lock solutions containing different concentrations of glycerol with either 0.5% or 0.85% saline in the presence of 1000 units/mL Heparin. FIG. 3b shows the hemocompatibility of catheter lock solutions containing different concentrations of glycerol with either 0.5% or 0.85% saline in the presence of 3.8% of sodium citrate.

Solutions containing either heparin or sodium citrate with less than 60% concentration of glycerol and at least 0.5% NaCl were found to be non-hemolytic and safe on erythrocytes. Thus, the hemocompatibility of glycerol solutions containing an anticoagulant was comparable to that of glycerol solutions alone, as in FIG. 1, in presence of at least 0.5% NaCl.

Therefore, a combination of 35-50% glycerol, 0.5-0.85% NaCl and anticoagulants like heparin or sodium citrate in a catheter lock solution would provide both the antimicrobial and antithrombogenic protection without causing significant hemolysis.

Example 6

Antimicrobial Effect of Catheter Lock Solution Containing Glycerol, Salt and Heparin as Determined by "Time to Kill" Assay To determine the antimicrobial performance of solutions containing 10-50% glycerol (w/w) and 0.85% NaCl (w/v) in presence of 1000 units/mL Heparin, "time to kill" experiments were carried out by following the method as described in Example 3.

Figure 4A:
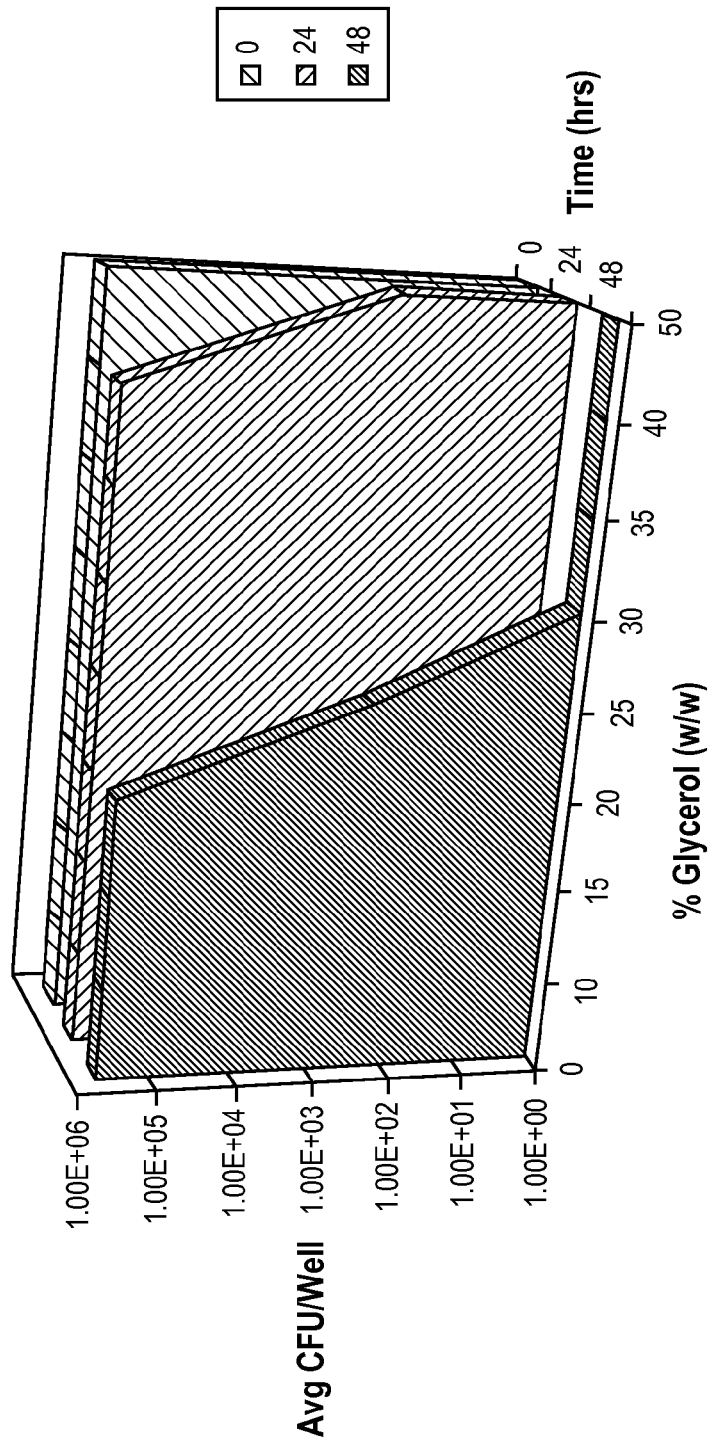
FIG. 4a is a chart showing the antimicrobial effect of solutions containing 0.85% NaCl and 10-50% glycerol in the presence of 1000 units/mL Heparin on planktonic *Acinetobacter baumannii* at 0, 24, and 48 hours.
Figure 4B:
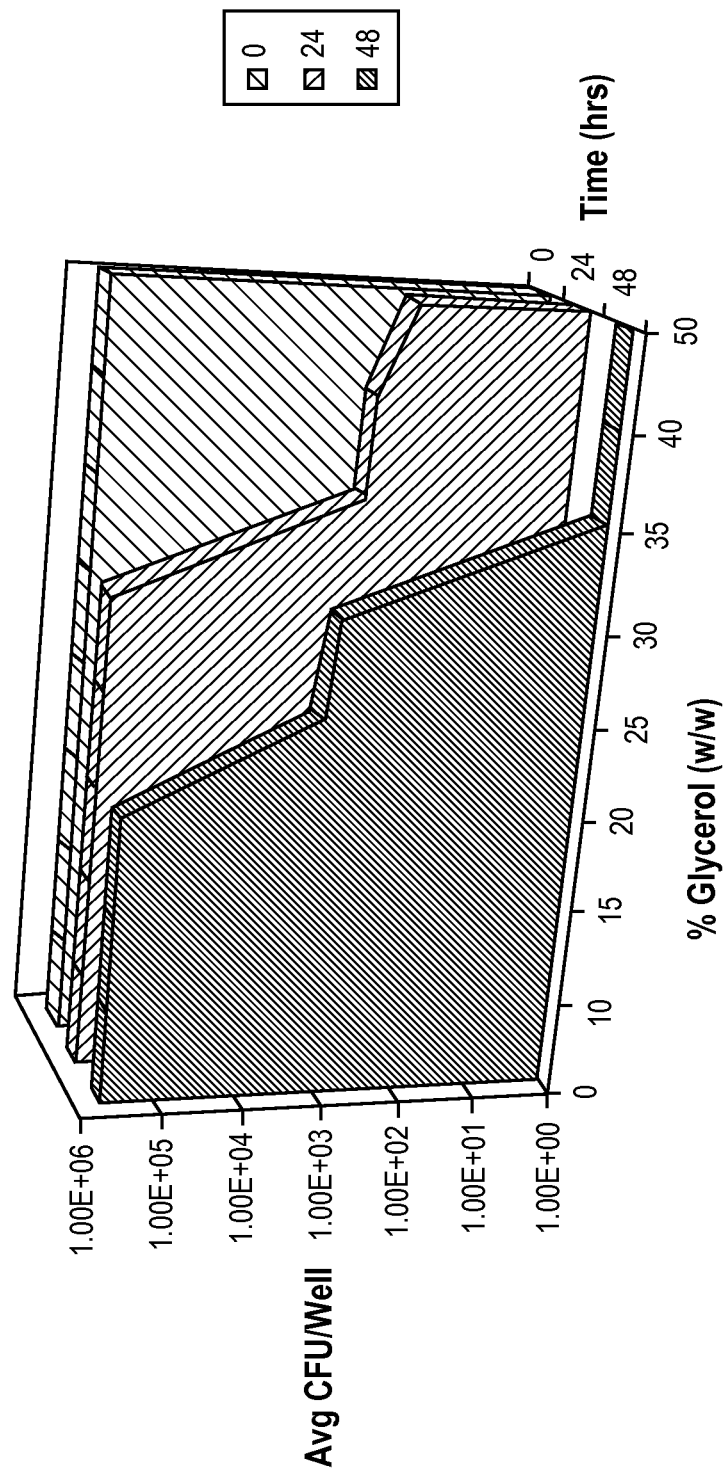
FIG. 4b is a chart showing the antimicrobial effect of solutions containing 0.85% NaCl and 10-50% glycerol in the presence of 1000 units/mL Heparin on planktonic *Enterobacter colacae* at 0, 24, and 48 hours.
Figure 4C:
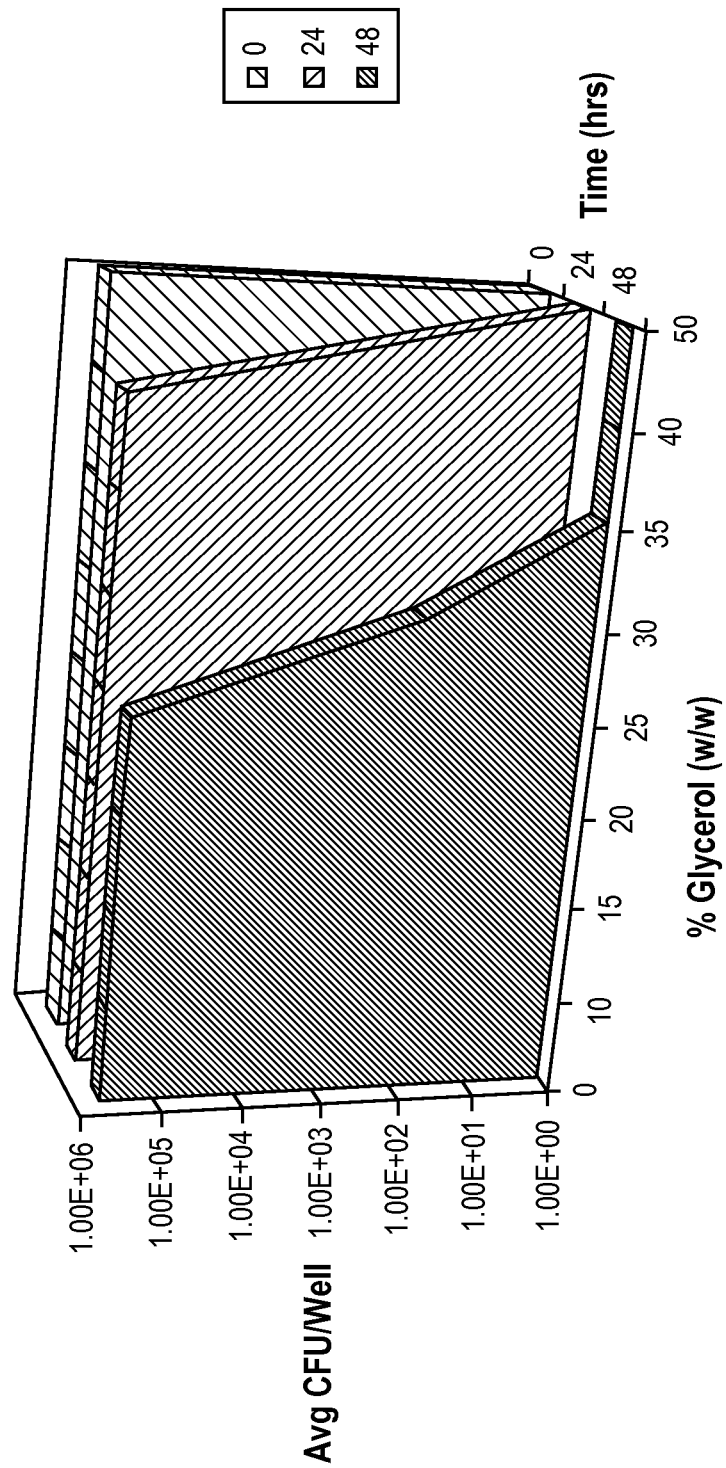
FIG. 4c is a chart showing the antimicrobial effect of solutions containing 0.85% NaCl and 10-50% glycerol in the presence of 1000 units/mL Heparin on planktonic *Pseudomonas aeruginosa* at 0, 24, and 48 hours.

FIGS. 4a, 4b, and 4c show the antimicrobial effect of solutions containing 10-50% glycerol in the presence of 1000 units/mL Heparin on planktonic *Acinetobacter baumannii*, *Enterobacter cloacae*, and *Pseudomonas aeruginosa*, respectively, at 0, 24, and 48 hours.

According to FIGS. 4a, 4b, and 4c, the presence of heparin did not affect the antimicrobial effect of glycerol. Solutions containing 35-50% glycerol, 0.85% NaCl and 1000 units/mL Heparin were able to eradicate all the three tested microorganisms.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for preventing catheter colonization by microbes and subsequent blood stream infection of a patient having an indwelling intravascular catheter, comprising:
   infusing a lock solution into a lumen of the catheter, the lock solution comprising glycerol at a bacteriostatic concentration range between about 40-60% w/w and sodium chloride at a concentration range between about 0.5-0.9% w/v.

2. The method of claim 1, further comprising placing a cap at an external end of the catheter.

3. The method according to claim 1, wherein the lock solution including an anticoagulant.

4. The method according to claim 3, wherein the anticoagulant is selected from the group consisting of di-ammonium hydrogen citrate, di-ammonium tartrate, N-(2-bis(carboxymethyl)aminoethyl)-N-(2-hydroxyethyl)glycin salt dihydrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O-bis(2-aminoethyl)-N,N,N,N-tetraacetic acid, N-(2-hydroxyethyl)ethylenediamine-N,N,N-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, tris(carboxymethyl)amine, heparin, warfarin, acetylsalicylic acid, ibuprofen, indomethacin, prostaglandins, sulfinpyrazone, streptokinase, urokinase, tissue plasminogen activator, coumarin, protamine sulfate, anti-thrombin III, coumadin, protein C/protein S, nicoumalone, phenprocoumon, hirudin, hirulog, glycosaminoglycans, and mixtures of the foregoing.

5. The method according to claim 1, wherein the lock solution includes an antimicrobial agent.

6. The method according to claim 5, wherein the antimicrobial agent is selected from a group consisting of hydrochloric acid, a taurinamide derivative, a phenol, quaternary ammonium surfactant, chlorine-containing, quinoline, quinaldinium, lactone, dye, thiosemicarbazone, quinone, sulfa, carbamates, urea, salicylamide, carbanilide, amide, guanide, amidine, chelate, imidazoline biocides, acetic acid, benzoic acid, sorbic acid, propionic acid, boric acid, dehydroacetic acid, sulfurous acid, vanillic acid, esters of p-hydroxybenzoic acid, ethanol, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4',5-tribromosalicylanilide, salicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver, nanosilver, silver sulfadiazine, silver nitrate, 5 fluorouracil, phenolic antiseptics, gentian violet, methylene blue, brilliant green, and bismuth compounds.

* * * * *